United States Patent [19]

Guzzi et al.

[11] 4,201,865
[45] May 6, 1980

[54] NOVEL PROSTAGLANDIN ANALOGUES

[75] Inventors: Umberto Guzzi; Romeo Ciabatti, both of Milan, Italy

[73] Assignee: Gruppo Lepetit S.p.A., Milan, Italy

[21] Appl. No.: 876,607

[22] Filed: Feb. 10, 1978

Related U.S. Application Data

[63] Continuation-in-part of Ser. No. 649,176, Jan. 15, 1976, abandoned.

[51] Int. Cl.² ............................................. C07C 177/10
[52] U.S. Cl. ...................................... 560/121; 424/305
[58] Field of Search ......................... 560/121; 562/503

[56] References Cited

U.S. PATENT DOCUMENTS 4,111,959  9/1978  Weiss ................................. 260/340.9

FOREIGN PATENT DOCUMENTS 50-70340  6/1975  Japan ....................................... 560/121

OTHER PUBLICATIONS

Sameleson, Advances in Prostaglandin and Thromboxane Research, pp. 483–491, (1978).

Primary Examiner—Robert Gerstl

[57] ABSTRACT

Novel prostaglandin analogues of the following general formula

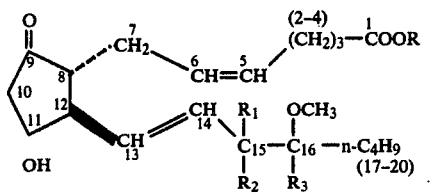

wherein R is an alkyl group from 1 to 4 carbon atoms, e.g. methyl, ethyl, propyl, isopropyl, butyl, isobutyl or tert-buytyl, $R_1$ is hydrogen, $R_2$ is hydroxy or $R_1$ and $R_2$ taken together represent a group oxo, $R_3$ is hydrogen or methyl. The new compounds have antisecretory utility.

3 Claims, No Drawings

NOVEL PROSTAGLANDIN ANALOGUES

CROSS REFERENCE TO RELATED APPLICATION

This application is a continuation-in-part of U.S. Pat. application Ser. No. 649,176 filed on Jan. 15, 1976, now abandoned.

SUMMARY OF THE INVENTION

This invention relates to novel prostaglandin-like compounds of the following general formula:

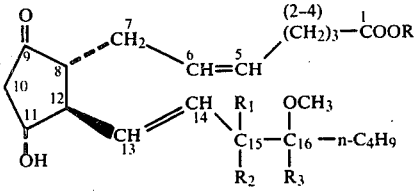

wherein R is an alkyl group having from 1 to 4 carbon atoms, $R_1$ is hydrogen, $R_2$ is hydroxy or $R_1$ and $R_2$ taken together represent a group oxo, $R_3$ is hydrogen or methyl. The expression "alkyl having from 1 to 4 carbon atoms" as used herein identifies a straight or branched alkyl radical selected from the group consisting of methyl, ethyl, propyl, isopropyl, butyl, isobutyl or tert-butyl.

The new compounds possess antisecretory utility.

The starting compounds for preparing the new product of this invention are cyclopentane aldehydes of the following general formula

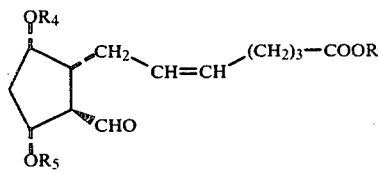

wherein R has the same meaning as before and $R_4$ and $R_5$ each independently represent hydrogen or a protecting group of the hydroxy function such as, for instance, lower alkyl of 1 to 6 carbon atoms, lower alkoxy-lower alkyl wherein the lower alkoxy and the lower alkyl portions have 1 to 6 carbon atoms, trityl, tetrahydropyran-2-yl, (4-lower alkoxy)-tetrahydropyran-4-yl, phenylcarbamyl, biphenylyl-carbamyl, terphenylylcarbamyl or an acyl radical selected from (1) alkanoyl of 2 to 8 carbon atoms (e.g. acetyl, propionyl, butyryl, isobutyryl, pentanoyl, pivaloyl, hexanoyl, heptanoyl, octanoyl;

(2) benzoyl or mono-substituted benzoyl wherein the substitunt is selected from chloro, bromo, fluoro, nitro, carbo(lower alkoxy), lower alkyl, lower alkoxy, phenyl-lower alkyl, (wherein "lower alkoxy" and "lower alkyl" have 1 to 4 carbon atoms), phenyl and cyclohexyl;

(3) lower alkoxy-carbonyl wherein "lower alkoxy" besides the terms having 1 to 4 carbon atoms includes also halogenated lower alkoxy radicals, e.g. 2,2,2-trichloroethoxy and 2,2,2-tribromoethoxy;

(4) phenoxycarbonyl;

(5) benzyloxycarbonyl and (6) biphenylyloxycarbonyl.

The above starting compounds may be prepared according to the method described in the literature. For instance, D.O.S. 2,217,930 and Belgian Pat. No. 807,161 disclose useful procedures for preparing those intermediates. The process for preparing the novel prostaglandin analogues according to the invention comprises as the first step the condensation between the aldehyde of formula II above and a phosphonate reagent of the following general formula

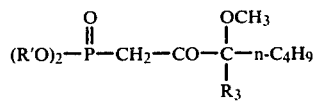

wherein $R_3$ has the same meaning as before and $R'$ is a lower alkyl of 1 to 5 carbon atoms. The aldehyde of formula II may be prepared just before to be contacted with the phosphonate III by cleavage of a corresponding acetal or similar derivative where the carbonyl function is protected.

The condensation between the aldehyde and the phosphorus reagent is carried out substantially under the same conditions which are widely described in the chemical literature concerning synthesis of prostaglandins from cyclopentane aldehyde precursors and phosphorus reagents. It is carried out in the presence of an anhydrous inert solvent such as tetrahydrofuran, dimethoxyethane, benzene, dioxane at a temperature between 0° C. and 80° C. However, the phosphonate reaction partner is first transformed into the corresponding anion by addition of about one equimolecular proportion of an alkali metal hydride.

Pursuant to this procedure, a prostaglandin-like derivative of the following general formula is obtained:

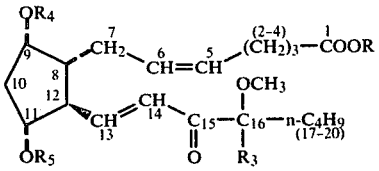

wherein R, $R_3$, $R_4$ and $R_5$ have the above meanings, which is then transformed into the end compounds of formula I by means of known procedures.

A preferred aspect of the invention comprises reacting the aldehyde of formula II wherein R is an alkyl group from 1 to 4 carbon atoms, $R_4$ is an alkanoyl of 2 to 8 carbon atoms and $R_5$ is hydrogen, with the anion of the phosphonate of formula III wherein $R'$ and $R_3$ are defined as above. The reaction is preferably carried out in dimethoxyethane as the reaction solvent and at a temperature between about 0° C. and about room temperature. The obtained compound of formula IV wherein R and $R_3$ are defined as above, $R_4$ is a $C_{2-8}$alkanoyl and $R_5$ is hydrogen, owing to the chirality center at $C_{16}$, may exist in two possible isomeric forms.

If desired, these forms may be separated by means of techniques well known to men skilled in the art, as an example by column or preparative thin layer chromatography, and possess the opposite absolute configuration (R or S). The two isomeric compounds or the mixture thereof are then treated with an appropriate reducing agent such as, for instance, sodium borohydride in order to reduce the oxo group at $C_{15}$ to hydroxy. This step causes the introduction of a further asimmetry center so that from each of the $C_{16}$ isomers another pair of isomers having the same configuration at $C_{16}$ and opposite configuration at $C_{15}$ are obtained. The four isomeric compounds can be represented by the following formula

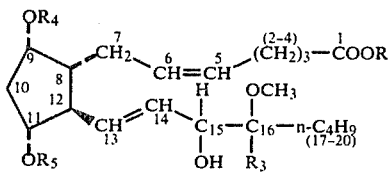

wherein R and $R_3$ are defined as above, $R_4$ is a $(C_{2-8})$alkanoyl and $R_5$ is hydrogen, and each of these isomeric compounds has at the correspondingly substituted carbons of the prostaglanding skeleton ($C_{15}$ and $C_{16}$) one of the following absolute configurations: (R,R), (R,S), (S,R) and (S,S).

These isomers may be separated from each other by means of known techniques, as an example, by column chromatography but, for the invention purposes, also a mixture of the possible isomers may be advantageously employed in the subsequent reaction steps, as the separation into the various isomeric forms may even be carried out once the end compounds of formula I are obtained. The reaction pathway comprises further protecting the hydroxy groups at the 11 and 15 positions of the compounds of the above formula V by reaction with an appropriate protecting agent, preferably 3,4-dihydro-2H-pyran, thus obtaining the corresponding 11,15-bis-tetrahydropyranyl ethers. A mild alkaline treatment, as an example by means of potassium carbonate in methanol, causes the hydrolysis of the $OR_4$ group at the position 9, whereby the so obtained 9-hydroxy derivative is transformed into the corresponding 9-keto compound by common oxidation procedures. Among the various oxidizing agents which can advantageously be employed, the Collins reagent ie., the complex pyridine/chromium oxide, is the most preferred one. An acidic hydrolysis occurring under mild conditions restores the free hydroxy groups at the 11 and 15 positions, whereby the end compounds of formula I are obtained. Preferably, the hydrolytic agent is a mixture of acetic acid, water and tetrahydrofuran in different proportions and the hydrolysis is advantageously carried out at a temperature of about 40° C. for a time varying from about 1 to about 24 hours.

The starting phosphorus reagents of formula III are prepared by condensing methylphosphonic acid lower alkyl esters with α-substituted carboxylic acids lower akyl esters (or the corresponding acid chlorides) according to the following reaction scheme:

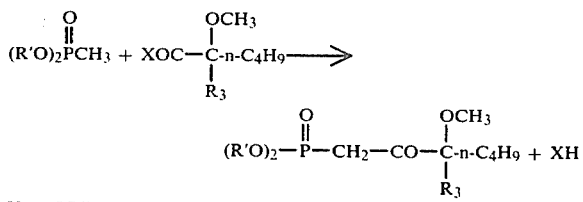

X = OR''; Cl wherein $R_3$ and R' have the same meaning as before and R'' represents an aliphatic radical of 1 to 5 carbon atoms. This procedure involves first transformation of the methyl phosphonates into the corresponding anion by addition of butyl lithium at $-78°$ C. in tetrahydrofuran and then contacting with the carboxylic acid ester (or the corresponding acid chloride) for about one hour at the same temperature.

The compounds of the invention possess antisecretory utility. More exactly, they were found to considerably inhibit the acidic gastric hypersecretion which, as it is known, is often responsible of gastric ulcers.

In the actual practice, the gastric antisecretory properties were evaluated on the basis of their effectiveness in inhibiting the hyperacidity induced by hystamine in dogs. Hystamine, which is a potent stimulator of the acidic gastric secretion (see Bertaccini et al. Eur. Journ. Pharmacol., 28, 360, 1974), was administered intravenously by continuous infusion during the experiments.

A group of four mongrel dogs weighing approximately 20 Kg was used in each experiments.

The dogs were surgically operated in the stomachs according to the method described by Bertaccini et al. (see above), in order to provide each animal with an innervated gastric fistula (G.F.) or main stomach, and a denervated Haidenhain pouche (H.P.).

The main stomach and the Haidenhain pouche were each equipped with a cannula in order to allow the gastric juices to drain to the exterior by gravity. The two surgically prepared cavities allow to determine if the antisecretory effect has to be ascribed to a direct action of the tested compounds on the oxyntic cells ie., the cells of the gastric walls secreting acidity, (inhibition of the hyperacidity produced both by G.F. and H.P.) or if it is mediated by the autonomous nervous system (inhibition of the hyperacidity produced only by G.F.). After a period of four to five weeks which was allowed to the animals for recovery, the dogs were administered intravenously with histamine in the amount of 160 micrograms of hystamine per kg. of body weight per hour (160 $\mu g\text{-}kg^{-1}h^{-1}$) in order to stimulate the acidic secretion both in the G.F. and in the H.P. The maximum secretory effect was reached after approximately 1 hour and the infusion of histamine was prolonged for approximately three further hours. During the whole period of infusion, the acidic output was collected every ten minutes and titrated by means of NaOH 0.1 to pH 7.0 on an automatic titrator (Radiometer, Copenhagen). The so-obtained values (mean of four dogs) were considered as the "control values". Food, but not water, was withheld 18 hours before each experiments. At the beginning, the dogs were administered with 160 $\mu g\ kg^{-1}h^{-1}$ of histamine. After reaching the maximum secretory value ie., approximately after 1 hour, the compound to be tested was administered intravenously at predetermined dosages per kg. of body weight during one hour, while the infusion of histamine at the above dosage was carried on. During this period the acidic output both from the G.F. and H.P. was collected every ten minutes and titrated as described above.

By means of the so obtained values (mean of four dogs) and the corresponding "control values" ie., the values obtained by determining the acidic output for one hour after the maximum secretory effect due to histamine was reached, it was possible to establish, by obvious calculations, the percent inhibition of the acidic gastric secretion both from the G.F. and the H.P. of the tested compounds versus the controls.

Representative experiments have shown that dosages varying from about 50 to about 100 μg/kg hour practically block the gastric hyperacidity induced by histamine both in the G.F. and in the H.P. This can be seen from the following table, wherein the results obtained by testing the compound of example 2 having $[\alpha]_D^{20}=-77.7$ (c=0.67% in CHCl$_3$) and the compound of example 5 having $[\alpha]_D^{20}=-45$ (c=0.46% in CHCl$_3$) are reported:

TABLE

| Compound of Example | $/\alpha/_D^{20}$ | μg kg$^{-1}$h$^{-1}$ | % inhibition of the acidic gastric secretion over the controls: | |
|---|---|---|---|---|
| | | | in the G.F. | in the H.P. |
| 2 | −77.7 | 10 | 25 | 25 |
| | | 25 | 50 | 50 |
| | | 50 | 95 | 95 |
| 5 | −45 | 10 | 20 | 20 |
| | | 50 | 55 | 55 |
| | | 100 | 100 | 100 |

This invention is illustrated by the following non limitative specific examples:

Example 1:
9α-Acetoxy-11α-hydroxy-16-methoxy-15-oxo-prosta-5(Z),13(E)-diene-1-oic-acid methyl ester (16R and 16S isomers)

(A) 1.3 Grams (30 m moles) of a 55% suspension of sodium hydride in mineral oil are washed under nitrogen atmosphere with hexane and then 20 ml of anhydrous dimethoxyethane are added thereto. To this suspension at a temperature of about 0° C., 8 g. (32 m moles) of the dimethyl ester of (3-methoxy-2-oxo-heptyl)phosphonic acid dissolved in 50 ml of anhydrous dimethoxyethane are added. After standing for 15 minutes at the room temperature the mixture is cooled to 0° C. and 6.24 g. of the methyl ester of 7-(5α-acetoxy-2β-formyl-3α-hydroxycyclopent-1α-yl)-5(Z)-hepten-1-oic acid (20 m moles), dissolved in 100 ml of anhydrous dimethoxyethane are added. The temperature is then allowed to raise to about 20° C. and the mixture is maintained under stirring for four hours. The reaction mixture is then poured into an aqueous solution saturated with NaH$_2$PO$_4$ which is subsequently extracted with ethyl acetate. The organic extract is evaporated to give 14.1 g. of a crude product containing two components. The two products which are the R and S isomers at the position 16 are separated by preparative thin layer chromatography by eluting first with ethyl ether/hexane 7:3 and then with ethyl ether/hexane 85:15. By this way, 1.38 g. of the less polar isomer and 1.410 g. of the more polar isomer are obtained.

The less polar isomer is an oily product having the following physical characteristics:

$[\alpha]_D^{20}=+85.4$(c=0.985% in CHCl$_3$)

U.V. absorption spectrum in methanol:

$\lambda$ max (mμ) 238, $E_1\ _{cm}^{1\%}=267$

I.R. absorption spectrum (neat:) the most significative absorption bands occur at the following frequencies (cm$^{-1}$):
3400, 2910, 2860, 1740 (sharp), 1625, 1440, 1370, 1240, 1100.

N.M.R. spectrum: the most significative absorption peaks in CDCl$_3$ occur at the following frequencies expressed in δ units:
0.88; 1.08–2.88; 2.03; 3.30; 3.64; 3.67; 3.83–4.32; 4.98–5.45; 6.50; 6.90. The mycroanalytical data are in agreement with the raw formula C$_{24}$H$_{38}$O$_7$. The more polar isomer is an oily product having the following physical characteristics:

$[\alpha]_D^{20}=+19.8$ (c=1.05 in CHCl$_3$)

U.V. absorption spectrum in methanol:

$\lambda$ max (mμ) 238, $E_1\ _{cm}^{1\%}=282$

I.R. absorption spectrum (neat): the most significative absorption bands occur at the following frequencies (cm$^{-1}$):
3450, 2920, 2860, 1730, 1700(sharp), 1620, 1435, 1370, 1320, 1240, 1100, 1040, 985.

N.M.R. spectrum: the most significative absorption peaks in CDCl$_3$ occur at the following frequencies expressed in δ units:
0.88; 1.07–2.84; 2.05; 3.30; 3.63; 3.67; 3.84–4.28; 4.98–5.45; 6.50; 6.90. The mycroanalytical data are in agreement with the raw formula C$_{24}$H$_{38}$O$_7$.

(B) The crude methyl ester of 7-(5α-acetoxy-2β-formyl-3α-hydroxy-cyclopent-1α-yl)-5(Z)-hepten-1-oic acid which is employed as the starting compound is prepared by following the procedure described in Belgian Pat. No. 807,161 for the close analog 7-[5α-(4-phenylbenzoyloxy)-2β-formyl-3α-hydroxy-cyclopent-1α-yl)]-5(Z)-hepten-1-oic acid methyl ester, the only difference consisting in the acylation of the 5α-hydroxy group on the cyclopentane ring with acetyl chloride instead of 4-phenylbenzoyl chloride. The corresponding precursors from which the above starting material is obtained by hydrolysis with 60% acetic acid is the methyl ester of 7-[5α-acetoxy-2β-dimethoxymethyl-3α-(tetrahydropyran-2-yloxy)-cyclopent-1α-yl)-]5(Z)-hepten-1-oic acid which is an oily having the following physical characteristics:

$[\alpha]_D^{20}=+26.5$ (c=1.02% in CHCl$_3$)

Example 2: 11α, 15-Dihydroxy-16-methoxy-9-oxo-prosta-5(Z),13(E)-diene-1-oic-acid methyl esters (pair of isomers: (15S, 16S) and (15R, 16S), or (15S, 16R) and (15R, 16R).

(A) To a solution of 1.3 g. of the less polar C$_{16}$-isomer obtained in Example 1 (ie., the product having $[\alpha]_D^{20}=+85.4$) in 150 ml of methanol are added dropwise at −10° C. 300 mg of NaBH$_4$ in 15 ml of ice water. The reaction mixture is stirred at −10° C. until the reaction is completed (the reaction course is followed by thin layer chromatography) and then it is poured into a saturated solution of NaH$_2$PO$_4$. Extraction with ethyl acetate and evaporation of the organic extract gives 1.15 g. of a mixture of isomeric 9α-acetoxy-11α,15-dihydroxy-16-methoxy-prosta-5(Z),13(E)-diene-1-oic acids methyl esters having the same absolute configuration at the position 16 and the opposite absolute configuration at the position 15. The N.M.R. spectrum and the microanalytical data are in agreement with the assigned structure.

This mixture is used as such for the subsequent reaction step.

(B) 1.35 Grams of the obtained mixture of isomeric 9α-acetoxy-11α-,15-dihydroxy-16-methoxy-prosta-5(Z),13(E)-diene-1-oic acid methyl esters dissolved in 75 ml of benzene and dried by azeotropic distillation, are treated with 9 ml of 3,4-dihydro-2H-pyran and 14 ml of anhydrous p-toluensulfonic acid. After 35 minutes the reaction mixture is neutralized with a solution of NaHCO$_3$ and extracted with ethyl ether. The organic extract is evaporated to give 1.5 grams of the corresponding 11α,15-bis-tetrahydropyranylether.

(C) 1.30 grams of 11α,15-bis-tetrahydropyranyl ether are dissolved in 50 ml of anhydrous methanol, then 800 mg. of anhydrous K$_2$CO$_3$ are added. The reaction mixture is stirred at room temperature for 24 hours after which period of time the reaction is generally completed. The reaction mixture is neutralized by adding a strongly acidic resin which is very easily eliminated by filtration. The filtrate is concentrated under vacuum to give 1.18 g of a mixture of two diastereoisomeric 9α-hydroxy-11α,15-bis[(tetrahydro-2H-pyran-2-yl)oxy]-16-methoxy-prosta-5(Z),13(E)-diene-1-oic acid methyl esters.

(D) To 4 g of Collins reagent (Py$_2$CrO$_3$) dissolved in 75 ml of anhydrous methylene chloride, 4 grams of celite and a solution of the previously described compound (1.18 g dissolved in 18 ml of anhydrous methylene chloride) are added.

The reaction mixture is stirred at room temperature for 30 minutes after which period of time the reaction is generally completed.

The reaction mixture is poured into 250 ml of ethyl ether, and then filtered and washed with water.

The organic phase is concentrated to dryness in vacuo. The oily residue is chromatographed on a silica gel column by eluting with ethyl ether:hexane with increasing proportions of ethyl ether to give 0.7 grams of the mixture of the two diastereoisomeric 11α,15-bis[-(tetrahydro-2H-pyran-2-yl)oxy]-9-oxa-16-methoxy-prosta-5(Z),13(E)-diene-1-oic acid methyl esters.

(E) The mixture obtained under (D) is dissolved in 110 ml of a solution of acetic acid:water:tetrahydrofuran (19:11:3). The reaction mixture is heated at 40° C. for 24 hours after which period of time the reaction is generally completed. The reaction mixture is saturated by adding NaCl and extracted with ethyl acetate. The organic phase is washed with water, dried and then concentrated in vacuo to give 0.530 of a mixture of the diastereoisomeric methyl esters of the title. They have the same absolute configuration at C$_{16}$ and the opposite absolute configuration at C$_{15}$. This mixture is chromatographed through an acid washed silica gel column by eluting with ethyl ether:hexane with increasing proportions of ethyl ether. The first eluted ester is an oil having the following characteristics:

$[\alpha]_D^{20} = -85$ (c=0.82%CHCl$_3$)

N.M.R. spectrum: the most significative absorption peaks in CDCl$_3$ occur at the following frequencies expressed in units:
3.47; 3.72; 3.8–4.5; 5.3–5.6; 5.7–5.9.

I.R. absorption spectrum (solution of CDCl$_3$): the most significative absorption bands occur at the following frequencies (cm$^{-1}$):
3470, 3005, 2950, 2925, 2870, 2240, 1740, 1600, 1455, 1438, 1405, 1245, 1220, 1155, 1090, 970.

The second eluted ester is an oil having the following characteristics:

$[\alpha]_D^{20} = -77.7$ (C=0.67%CHCl$_3$)

N.M.R. spectrum: the most significative absorption peaks in CDCl$_3$ occur at the following frequencies expressed in δ units:
3.43; 3.68; 3.9–4.4; 5.2–5.5; 5.6–5.8.

I.R. absorption spectrum (neat): the most significative absorption bands occur at the following frequencies (cm$^{-1}$):
3400, 3005, 2950, 2930, 2870, 2240, 1740, 1455, 1440, 1405, 1250, 1220, 1155, 1090, 970.

Example 3:
9α-Acetoxy-11α-hydroxy-16-methoxy-16-methyl-15-oxo-prosta-5(Z),13(E)-diene-1-oic acid methyl ester (16R and 16S isomers)

The two title products are obtained in the same way as described in the Example 1 by employing 1,2 g. of NaH (55% suspension in mineral oil) in 60 ml of dimethoxyethane, 8.65 g. of dimethyl ester of (3-methyl-3-methoxy-2-oxo-heptyl)phosphonic acid in 60 ml of dimethoxyethane and 5 g. of 7-(5α-acetoxy-2β-formyl-3α-hydroxy-cyclopent-1α-yl)-5(Z)-hepten-1-oic acid methyl ester in 45 ml of dimethoxyethane.

The two products are the R and S isomers at the C$_{16}$ and are separated in the same way as described in Example 1.

The less polar isomer (2.5 g) is an oil having the following characteristics:

$[\alpha]_D^{20} = +58.7$ (C=0.98% in CHCl$_3$)

N.M.R. spectrum: the most significative absorption peaks in CDCl$_3$ occur at the following frequencies expressed in δ units:
1.28; 2.06; 3.20; 3.67; 3.8–4.3; 5.0–5.5; 6.7–7.0.

The more polar product is an oil having the following characteristics:

$[\alpha]_D^{20} = +26.8$ (C=0.86% in CHCl$_3$)

N.M.R. spectrum: the most significative absorption peaks in CDCl$_3$ occur at the following frequencies expressed in δ units:
1.28; 2.06; 3.18; 3.66; 3.8–4.3; 5.0–5.5; 6.6–6.70.

Example 4:
9α,11α,15-Trihydroxy-16-methoxy-16-methyl-prosta-5(Z),13(E)-diene-1-oic acid methyl esters [isomers (15S, 16S), (15R, 16S), (15R, 16R), (15S, 16R)]

(A) 2.31 Grams of the more polar product obtained according to Example 3 ($[\alpha]_D^{20} = +26.8$) are reduced with NaBH$_4$ as described in Example 2 A) and after chromatographic separation the two 9α-acetate precursors of the title compounds are partially hydrolized by treatment with K$_2$CO$_3$ and methanol at room temperature for 20 hours.

The two products obtained are diastereoisomeric 9α,11α,15-trihydroxy-16-methoxy-16-methyl-prosta-5(Z),13(E)-diene-1-oic acid methyl ester having the same absolute configurations at the C$_{16}$ and the opposite absolute configuration at C$_{15}$. The two products are purified by chromatography through an acid washed silica gel column, by eluting with ethyl ether/hexane. The less polar product (310 mg) is an oil having the following characteristics:

N.M.R. spectrum; the most significative absorption peaks in CDCl₃ occur at the following frequencies expressed in δ units:
1.07; 3.23; 3.67; 3.8–4.3; 5.2–5.7.

$[\alpha]_D^{20} = +6.4$ (C=2.67% CHCl₃)

The more polar product (220 mg) is an oil having the following characteristics:

$[\alpha]_D^{20} = +50$ (C=0.8% CHCl₃)

N.M.R. spectrum: the most significative absorption peaks in CDCl₃ occur at the following frequencies expressed in δ units:
1.07; 3.23; 3.68; 3.8–4.3; 5.2–5.65

(B) By operating as described under paragraph A but utilizing as the starting material 1.5 g of the less polar product obtained according to Example 3 ($[\alpha]_D^{20} = +58.7$) the following couple of diastereoisomeric compounds having the same absolute configuration at C₁₆ and the opposite absolute configuration at C₁₅ is obtained.

The less polar product (500 mg) is an oil having the following characteristics:
N.M.R. spectrum: the most signficative absorption peaks in CDCl₃ occur at the following frequencies expressed in δ units:
1.12; 3.25; 3.67; 3.3–4.3; 5.3–5.8.

$[\alpha]_D^{20} = +9.9$ (C=2.2% CHCl₃)

The more polar product (300 mg) is an oil having the following characteristics:
N.M.R. spectrum: the most significative absorption peaks in CDCl₃ occur at the following frequencies expressed in δ units:
1.1; 3.25; 3.68; 3.8–4.3; 5.3–5.8.

$[\alpha]_D^{20} = +23.3$ (C=1.33%CHCl₃)

Example 5:
11α,15-Dihydroxy-16-methyl-16-methoxy-9-oxo-prosta-5(Z), 13(E)-diene-1-oic acid methyl esters [isomers (15S, 16S), (15R, 16S), (15S, 16R), (15R, 16R)].

(A) 310 Milligrams of the 9α-acetate precursor of the more polar product of paragraph A, Example 4 ($[\alpha]_D^{20} = +50$), are dissolved in 30 ml of benzene and dried by azeotropic distillation. To the dried product are added 1 ml of 3,4-dihydro-2H-pyran and 30 mg of p-toluenesulfonic acid. After 15 minutes the reaction is generally completed. The reaction mixture is neuralized by shaking with a solution of NaHCO₃ and washed with water. The organic phase is concentrated to dryness under vacuo to give a residue of 400 mg of the 11α,15-bis-tetrahydropyranyl ether derivative. To this product dissolved in 100 ml of anhydrous methanol are added 400 mg of anhydrous K₂CO₃. After 24 hours the reaction mixture is neutralized by addition of acidic resin, and filtered. The filtrate is concentrated to dryness under vacuo to give 360 mg of 9α-hydroxy-11α,15-bis-[(tetrahydropyran-2-yl)oxy]-16-methyl-16-methoxy-prosta-5(Z),13(E)-diene-oic acid methyl ester. To 50 ml of anhydrous methylene chloride are added, under mechanical stirring, 2.5 g. of Collins reagent (Py₂CrO₃), 2 g. of celite and 360 mg of the compound previously obtained.

After 2 hours the reaction mixture is poured into 200 ml of ethyl ether, filtered, and washed with a solution of NaHCO₃ and with water. The ethereal phase is concentrated under vacuo to give a residue of 350 mg of 11α,15-bis[(tetrahydropyran-2-yl)oxy]-16-methyl-16-methoxy-9-oxo-prosta-5(Z), 13(E)-diene-1-oic acid methyl ester.

150 Milligrams of the compound previously obtained are dissolved in 2 ml of a mixture of CH₃COOH, H₂O, THF(19:11:3) and heated at 40° C. for 2 hours. After this period of time the reaction mixture is neutralized with solid NaHCO₃ and extracted with ethyl ether. The organic phase is concentrated in vacuo to dryness to give a residue that is chromatographed on an acid washed silica gel column. The compound obtained is one of the four isomeric esters of the title and has the following characteristics:

$[\alpha]_D^{20} = -45$ (C=0.46% in CHCl₃)

(B) By following the same procedure described under paragraph A, from 630 mg of the less polar 9α-acetate precursor of the product of paragraph A, Example 4, ($[\alpha]_D^{20} = +6.4$), 400 mg of one of the four isomeric title products are obtained. This product has:

$[\alpha]_D^{20} = -60.6$ (C=1.15% in CHCl₃)

(C) By following the same procedure described under paragraph A, from 600 mg of the less polar 9α-acetate precursor of the product of paragraph B, Example 4, ($[\alpha]_D^{20} = +9.9$) 400 mg of one of the four isomeric title products are obtained.
This product has:

$[\alpha]_D^{20} = -62$ (C=2.52% in CHCl₃)

(D) By following the same procedure described under paragraph A, from 700 mg of the more polar 9α-acetate precursor of the product of paragraph B, Example 4, ($[\alpha]_D^{20} = +23.3$), 420 mg of one of the four isomeric title products are obtained. This product has:

$[\alpha]_D^{20} = -48$ (C=1.02% in CHCl₃)

We claim:
1. Compounds of formula

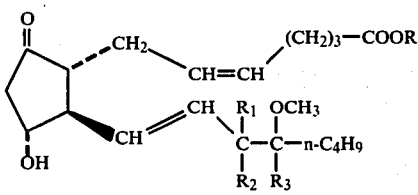

wherein R is an alkyl group having from 1 to 4 carbon atoms, R₁ is hydrogen, R₂ is hydroxy or R₁ and R₂ taken together represent a group oxo, R₃ is hydrogen or methyl.

2. A compound as in claim 1, which is 11α, 15-dihydroxy-16-methoxy-9-oxo-prosta-5(Z), 13(E)-diene-1-oic acid methyl ester.

3. A compound as in claim 1, which is 11α,15-hydroxy-16-methoxy-16-methyl-9-oxo-prosta-5(Z), 13(E)-diene-1-oic acid methyl ester.

* * * * *